United States Patent
Zhang et al.

(10) Patent No.: US 11,678,871 B2
(45) Date of Patent: Jun. 20, 2023

(54) BALLOON PULLING DEVICE AND MANUFACTURING METHOD THEREFOR

(71) Applicant: Shanghai Keci Medical Technology Co., LTD, Shanghai (CN)

(72) Inventors: Zhichao Zhang, Shanghai (CN); Chuanhai Zhang, Shanghai (CN)

(73) Assignee: SHANGHAI KECI MEDICAL TECHNOLOGY CO., LTD, Shanghai (CN)

( * ) Notice: Subject to any disclaimer, the term of this patent is extended or adjusted under 35 U.S.C. 154(b) by 0 days.

(21) Appl. No.: 16/976,407

(22) PCT Filed: Aug. 30, 2018

(86) PCT No.: PCT/CN2018/103279
§ 371 (c)(1),
(2) Date: Aug. 27, 2020

(87) PCT Pub. No.: WO2019/165772
PCT Pub. Date: Sep. 6, 2019

(65) Prior Publication Data
US 2021/0113202 A1     Apr. 22, 2021

(30) Foreign Application Priority Data
Feb. 27, 2018   (CN) .......................... 201810165074.9

(51) Int. Cl.
*A61B 17/02* (2006.01)
*A61B 17/00* (2006.01)

(52) U.S. Cl.
CPC    *A61B 17/0218* (2013.01); *A61B 2017/00526* (2013.01); *A61B 2017/00557* (2013.01)

(58) Field of Classification Search
CPC combination set(s) only.
See application file for complete search history.

(56) References Cited

U.S. PATENT DOCUMENTS

| | | | |
|---|---|---|---|
| 4,763,654 A | 8/1988 | Jang | |
| D303,288 S | 9/1989 | Harboe | |
| 4,862,886 A | 9/1989 | Clarke | |
| 5,147,377 A | 9/1992 | Sahota | |
| D360,260 S | 7/1995 | Brandt | |
| D390,659 S | 2/1998 | Chan | |
| 7,837,672 B2 * | 11/2010 | Intoccia | A61B 17/22 604/540 |

(Continued)

FOREIGN PATENT DOCUMENTS

| CN | 103055411 A | 4/2013 |
|---|---|---|
| CN | 103442650 A | 9/2013 |

(Continued)

*Primary Examiner* — Sameh R Boles

(57) ABSTRACT

A balloon pulling device, comprising a core tube (11) portion and a balloon (12) portion, wherein the core tube (11) portion may inflate and deflate the balloon (12) portion by using a fluid; the present invention is characterized in that the balloon (12) portion comprises a plurality of expansion segments (13), the expansion segments (13) being larger than the remaining portion of the balloon (12) after being inflated with a fluid such that the entire balloon (12) forms a curved contour. A simple and reliable balloon pulling device capable of retracting at a long distance while being finely adjusted is achieved.

10 Claims, 4 Drawing Sheets

(56) References Cited

U.S. PATENT DOCUMENTS

| | | |
|---|---|---|
| 8,795,312 B2 | 8/2014 | Fan et al. |
| 9,439,705 B2 | 9/2016 | Fan et al. |
| D851,245 S | 6/2019 | Baxter |
| 10,463,468 B2 | 11/2019 | Janardhan |
| D879,958 S | 3/2020 | Li et al. |
| 2006/0085022 A1 | 4/2006 | Hayes |
| 2008/0306583 A1 | 12/2008 | Bashiri |
| 2008/0312589 A1 | 12/2008 | Dlugos |
| 2012/0150210 A1 | 6/2012 | Fan et al. |
| 2014/0012304 A1 | 1/2014 | Lampropoulos |
| 2014/0066939 A1* | 3/2014 | Kaiser ................ A61B 17/562 606/90 |
| 2014/0243875 A1 | 8/2014 | Chen |
| 2014/0309646 A1 | 10/2014 | Fan et al. |
| 2015/0342590 A1 | 12/2015 | Cantillon-Murphy et al. |
| 2017/0150957 A9 | 6/2017 | O'Shea et al. |

FOREIGN PATENT DOCUMENTS

| | | |
|---|---|---|
| CN | 104189989 A | 12/2014 |
| CN | 201333252 Y | 8/2015 |
| CN | 204581372 U | 8/2015 |
| CN | 2120592 U | 9/2015 |
| CN | 104921853 A | 9/2015 |
| CN | 105997161 A | 10/2016 |
| CN | 106422038 A | 2/2017 |
| CN | 304614456 | 5/2018 |
| CN | 305072250 | 3/2019 |
| JP | D1637001 | 7/2019 |
| WO | WO 2014096370 A2 | 6/2014 |
| WO | WO2016/077358 A1 | 5/2016 |
| WO | WO216160589 A1 | 10/2016 |

* cited by examiner

BALLOON PULLING DEVICE AND MANUFACTURING METHOD THEREFOR

TECHNICAL FIELD

The present invention relates to the field of medical equipment, in particular to a balloon pulling device and a manufacturing method thereof.

BACKGROUND TECHNIQUE

Retractors, also known as pull hooks, are used to retract tissues, reveal the scope of surgery, and facilitate exploration and operation. They can be divided into hand-held retractors and automatic retractors. There are various specifications of different shapes and sizes, and the appropriate retractor can be selected according to the needs of the operation.

The traditional retractor requires a large operating space, which requires a large surgical wound. At the same time, traditional retractors are mostly made of metal and have sharp ends, which are likely to cause secondary trauma to patients and damage important organs.

The catheter retractor is used for tissue retraction during surgery and the product can complete the retraction operation through natural cavity intervention or open surgical intervention. Surgery includes, but is not limited to, various types of laparoscopic surgery, cardiovascular surgery, brain surgery, gastrointestinal surgery, urinary disease surgery, etc. The tissues to be retracted include but are not limited to gastrointestinal tract, esophagus, airway, urethra, vagina, bladder, etc. The purpose of retraction includes but is not limited to protecting specific tissues and removing specific tissues to facilitate surgical operations.

A balloon catheter retractor as shown in FIG. 1, comprising: a catheter 5 with an air valve at one end, a balloon 4 arranged on the periphery of the catheter 5, one or more cavities in the catheter, and the catheter part of the tube is inflated or deflated, and the balloon 4 will bend to one side when inflated. The material of the balloon 4 is non-compliant, and the two ends 3 are sealed on the catheter 5 by laser welding.

However, the curved balloon shown in FIG. 1 uses a single balloon, which places higher requirements on the material and degree of curvature of the balloon. Only by accurately calculating and testing the balloon material can the retraction of a specific operation be achieved. Distance requirements. This brings difficulties to the preparation of such curved balloons and puts forward higher technical requirements. In some specific operations, the curvature of a single balloon may not achieve the required retraction distance.

Therefore, how to prepare a curved balloon so that it can be bent naturally after inflation is the key to the realization of this invention.

SUMMARY OF THE INVENTION

The purpose of the present invention is to provide a curved balloon for natural channel intervention or open surgical intervention to complete the retraction operation based on the above-mentioned problems, which solves the problem that the current catheter retractor has complex structure, inconvenient operation, and large product diameter and cannot pass through. The narrow, complicated structure of the cavity, the inability to accurately control the pulling force, the low reliability and other problems, the present invention realizes a simple and reliable balloon pulling device that can realize a larger distance and can be precisely adjusted.

In order to achieve the above objective, the present invention provides a balloon pulling device, which includes a core tube and a balloon part. The core tube part can inflate and release fluid to the balloon part. The balloon part is characterized in that the balloon part includes several expansion sections. The inflation section is larger than the rest of the balloon after being filled with fluid, so that the entire balloon is bent.

The core tube is flexible and has a plurality of long strips of cavities therein. There is at least one hole on the surface of the core tube, or there is a corresponding hole for each expansion section, encapsulated or attached to the core tube. The axis of the balloon is on one side of the axis of the core tube. The core tube can be a number of independent core tubes, each core tube individually or separately controls the inflation or charging and discharging of several balloon inflation or expansion segments; or it can also be a multi-lumen tube, each tube individually controlling the inflation or charging and discharging of several balloon inflation or expansion segments.

There can also be several balloons on the core tube, and each balloon has multiple expansion sections, so that each balloon can be individually controlled to bend or each balloon can individually control the bending. The two ends of the balloon are connected with a wire-like material with low ductility.

The recommended parameters of the balloon can be any one or several of the following groups: The length of the expanded section of the balloon is greater than its outer diameter in the unexpanded state. The adjacent intervals between the inflation or expanded segments of the balloon are less than 0.2 times the length of the inflation or expanded segments.

How to prepare a curved balloon so that it can bend naturally after inflation is a key issue in achieving balloon traction. In order to achieve this objective, the present invention also provides a method for manufacturing a balloon pulling device, which includes the following steps: using a splicing mold or die to make the material form a balloon on the balloon forming machine; after cooling, the mold is removed and the balloon is taken out; The cavity core tube is bored and punched in the core tube; the balloon is placed in a preset or predetermined position, and the balloon is fixed on the core tube by welding or glue bonding.

Among them, the mold is divided into two parts, and the shape of the inner or internal cavity after the splicing of the two petal molds is consistent with the final outer contour of the balloon. Cooling is by external water cooling until it is consistent with the ambient temperature. The core tube is extruded by an extruder to form a single-lumen or multi-lumen tube.

The manufacturing method also includes after fixing the balloon to the core tube, using a wire-like or ductile material with low ductility, fixing one end near the distal end of the core tube, and fixing the other end near the proximal end of the core tube, and then combining the filament material with core tube by bonding.

The filamentous or filamentary material can be a metal that is not easily ductile, that is, a metal with a larger modulus. Preferably, the two ends of the metal wire are fixed near the distal end of the core tube, that is, the distal end of the balloon, and near the proximal end of the core tube, that is, the proximal end of the balloon.

There can be one or more balloons fixed on the core tube. In the case of multiple balloons, the core tube should be a multi-lumen tube or a combination of multiple single-lumen tubes, and each balloon has at least one corresponding to the core tube. The opening at the location is used to charge and discharge fluid.

The invention realizes a simple and reliable balloon pulling device that can realize a larger distance of retraction and can be accurately or precisely adjusted.

In order to make the above-mentioned objects, features and advantages of the present invention more obvious and understandable, preferred embodiments are described below in detail with accompanying drawings.

DESCRIPTION OF THE DRAWINGS

In order to more clearly illustrate the specific embodiments of the present invention or the technical solutions in the prior art, the following will briefly introduce the drawings to be used in the specific embodiments or the description of the prior art, and obviously, the attached following description. The drawings are some embodiments of the present invention, and those skilled in the art can obtain other embodiments based on these drawings without creative work.

DETAILED DESCRIPTION

Figure 1:
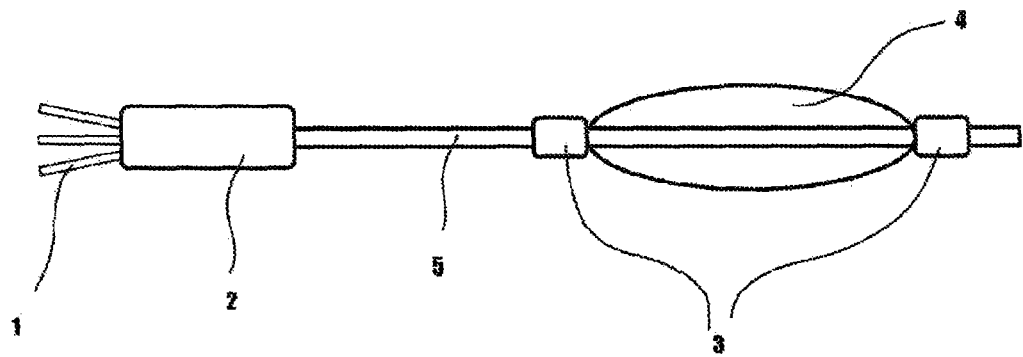
FIG. 1 is a schematic diagram of a conventional balloon pulling device.

The technical solutions in the embodiments of the present invention will be clearly and completely described below in conjunction with the accompanying drawings in the embodiments of the present invention. Obviously, the described embodiments are only a part of the embodiments of the present invention, rather than all the embodiments. The components of the embodiments of the present invention generally described and illustrated in the drawings herein may be arranged and designed in various different configurations. Therefore, the following detailed description of the embodiments of the present invention provided in the accompanying drawings is not intended to limit the scope of the claimed invention, but merely represents selected embodiments of the present invention. Based on the embodiments of the present invention, all other embodiments obtained by those skilled in the art without creative work shall fall within the protection scope of the present invention.

In view of the problem of insufficient curvature of the balloon in the prior art and the inability to perform precise bending to meet various surgical traction displacements, the present invention proposes the idea of forming a balloon into multiple expansion sections connected in series, and each expansion section is, after being filled with fluid and expanded, squeezed to form a bend. In the case of a balloon, both the inflated or expanded section and the non-inflated or non-expanded section will inflate after the overall inflation or filling. The expansion section and the non-expansion section are pressed against each other, or will squeeze each other, and because of the eccentricity, the entire axis of the balloon is elongated, and the axis of the core tube is elongated very little, resulting in bending.

In the multi-balloon scheme, the first balloon inflation and second balloon inflation will squeeze each other, which will cause the whole to bend, but under this bending scheme, the rigidity of the hollow between the first balloon and the second balloon is very low, so it suffers from external interference. It's easy to straighten. It is also possible to use multiple such balloons to accumulate or to achieve greater bending or to achieve bending of different shapes.

The present invention will be described in further detail below, so that those skilled in the art can implement it with reference to the description text.

Figure 2:
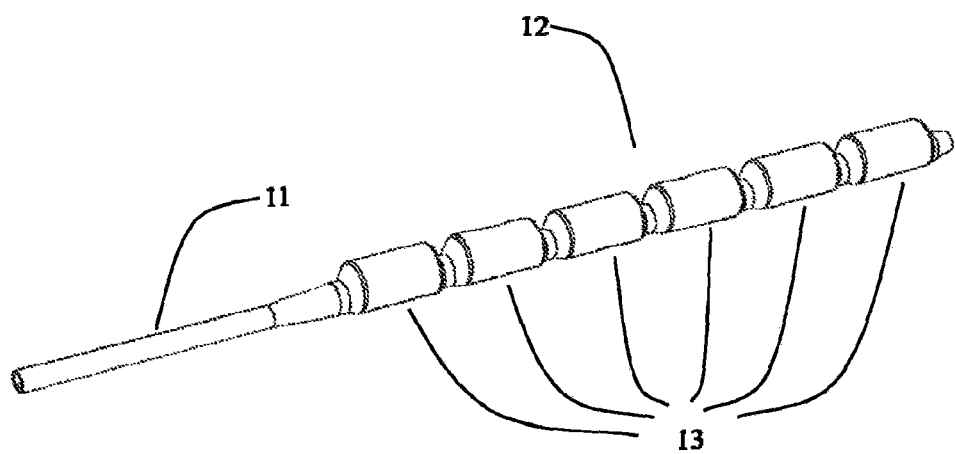
FIG. 2 is a schematic diagram of the balloon pulling device of the present invention.

First, please refer to FIG. 2, which is a schematic diagram of the balloon pulling device of the present invention.

The balloon pulling device as shown in FIG. 2 mainly consists of two parts, a core tube or core catheter 11 and a balloon 12 covering the core tube or core catheter 11. The balloon 12 includes a plurality of expansion segments or sections 13, and a plurality of non-expandable parts located between the expansion sections 13. The balloon 12 is located at the middle and rear end of the core tube 11. The core tube 11 is a tube having a hollow lumen. Because it needs to be inserted into the patient's body and can be pulled by the balloon 12, the core tube 11 is usually a long, flexible plastic or plastic tube with good biocompatibility. The core tube 11 can fill and discharge the balloon 12 with fluid. FIG. 2 is a state not filled with fluid. In this state, the expansion section 13 has not yet expanded, which is slightly larger than the non-expansion section.

Figure 3:
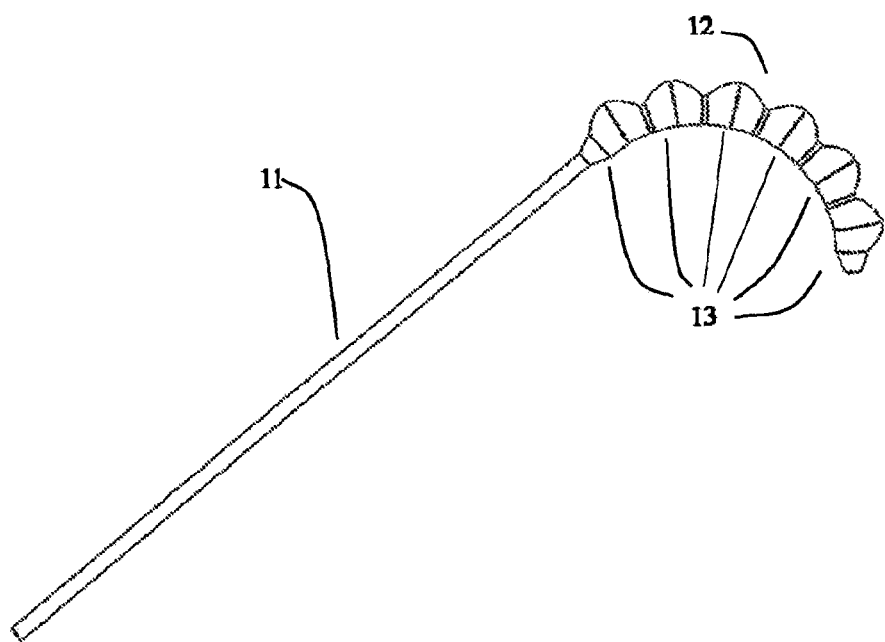
FIG. 3 is a schematic diagram of the balloon pulling device of the present invention filled with fluid.

The inflation or expansion section 13 is larger than the rest of the balloon 12 after being filled with fluid. After each inflation section 13 is filled with fluid, it squeezes or is pressed together with the non-inflation or non-expanded section, so that the entire balloon 12 is bent. Please refer to FIG. 3, which is a schematic diagram of the balloon retractor or pulling device of the present invention filled with fluid. In FIG. 3, each expansion section 13 of the balloon 12 is filled with fluid to expand and squeeze or press against each other to form a curved profile. Because the axis of the balloon 12 does not coincide with the axis of the core tube 11, the axis of each expansion section 13 is located on one side of the core tube 11, so that each expansion section 13 will accumulate the degree of bending after being filled with fluid, that is, expansion. The more segments 13 there are, the longer it is, and the more they deviate from the axis of the core tube 11, the greater the degree of accumulated bending, and the greater the pulling distance. Therefore, the degree of pulling can be estimated and simulated by controlling the length, number, and degree of eccentricity of the expansion sections 13, so as to achieve a large pulling distance range while accurately fine-tuning the pulling position and distance.

In other embodiments, there may be multiple balloons 12 on the core tube 11, and each balloon 12 has multiple expansion sections 13, so that each balloon 12 can individually control the bending of a part of the core tube 11 shape.

Figure 4:
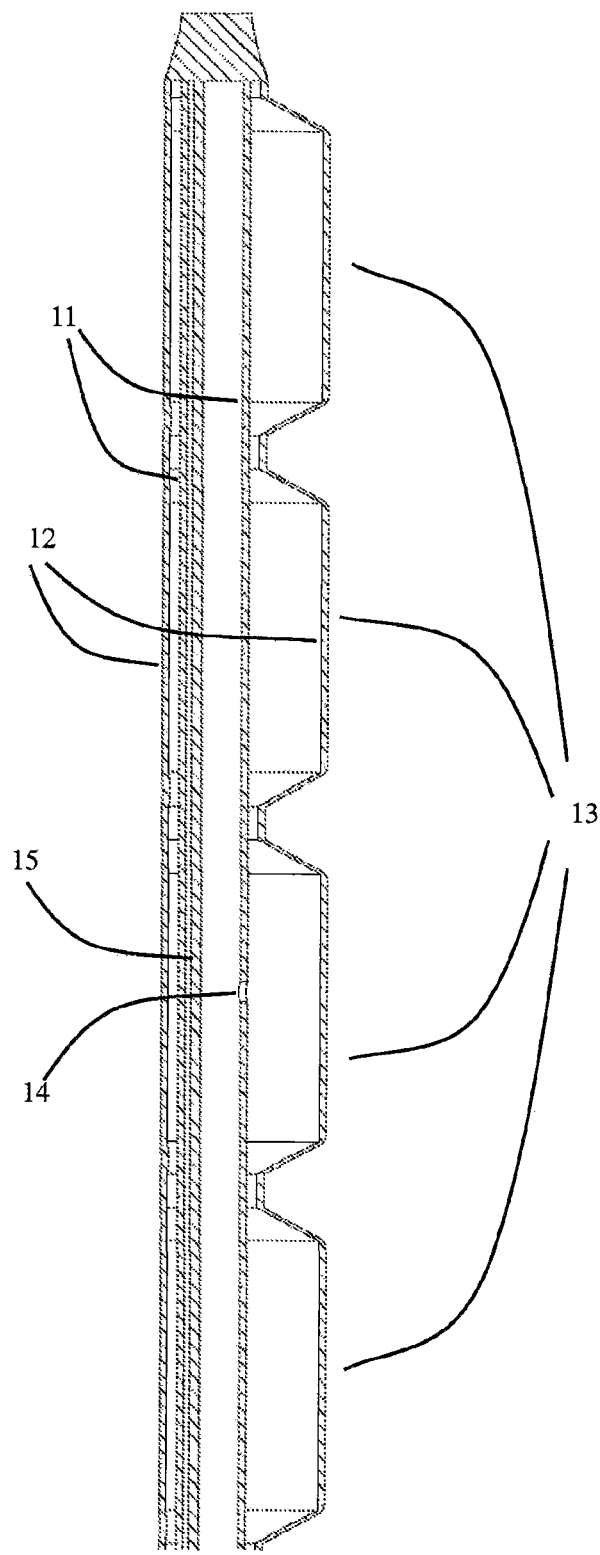
FIG. 4 is a cross-sectional view of the balloon pulling device of the present invention.
Figure 5:
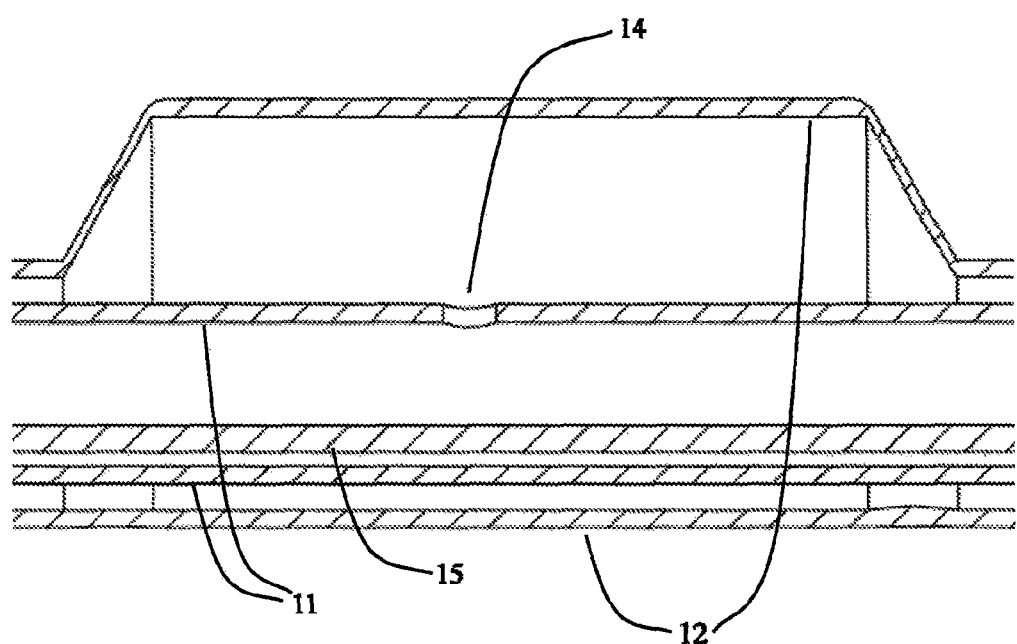
FIG. 5 is a partial enlarged view of the cross-section of the balloon pulling device of the present invention.

Next, please refer to FIGS. 4 and 5. FIG. 4 is a cross-sectional view of the balloon retractor or pulling device of the present invention, and FIG. 5 is a partial enlarged view of the cross-sectional view of the balloon retractor of the present invention. In FIGS. 4 and 5, it can be seen that the core tube 11 has holes 14 on the surface covered by the balloon 12 or has corresponding holes 14 for each expansion section 13. The core tube 11 can be a plurality of independent core tubes 11, each core tube 11 individually controls the inflation and discharging of the inflation section 13 of a single balloon 12; it can also be a multi-lumen tube, each of which individually controls a single balloon 12 charge and discharge, or expansion and contraction, of the expansion section 13. The inflation or expansion sections 13 of the balloon 12 may be connected to or in communication with each other through a non-inflatable section, or may be various independent and disconnected inflated sections, for example, composed of multiple independent small inflatable balloons or each section of the non-inflated section is tightly tied. Both ends of the balloon may be connected with a wire-like material 15 with low ductility. The filamentary material 15 may be disposed in the lumen of the core tube 11 as shown in FIG. 5, or may be disposed on the outer surface of the core tube. The filamentary material 15 is made of a metal material with a relatively large modulus, such as metal, to ensure that the corresponding part of the core tube will not be elongated when the balloon 12 is inflated, thereby reducing the degree of bending and causing deformation of the core tube.

The length of the inflation or expanded section 13 of the balloon 12 is greater than the outer diameter of the uninflated or unexpanded state. The adjacent interval between the expansion sections 13 of the balloon 12 is less than 0.2 times the length of the expansion section 13.

In actual use, in the unfilled state, the balloon retractor or pulling device is extended into the patient's lumen (minimally invasive lumen or natural lumen), and part of the fluid is first filled (preferably, the internal pressure is between 1-4 atmospheric pressure), and the distal balloon 12 will be visibly bent. The imaging device is used for positioning, and the handle is rotated and pushed to make the angle and position of the device reach the desired state. Then continue filling the device with liquid (preferably, the internal pressure of the device reaches between 4-6 atmospheres), and the balloon 12 will remain bent to the maximum extent, thereby achieving the purpose of pulling away the target tissue.

How to prepare a curved balloon so that it can bend naturally after inflation is a key issue in achieving balloon traction. In order to achieve this objective, the present invention also provides a method for manufacturing a balloon retractor or pulling device including the following steps:

The following is the preparation method of this type of balloon:

In the case of a single balloon, a thermoplastic polymer material is selected, melted and extruded into a barrel or material tube. Milling the balloon forming mold, the mold is divided into two halves, and the shape of the inner cavity after the two mold halves are spliced is consistent with the final outer contour of the balloon 12. The spliced mold is placed on the balloon forming machine, and the material tube is placed in the cavity. Set the molding temperature, molding internal pressure and stretching rate, stretch and expand the material tube so that the outer wall of the final material tube is adhered or applied to the inner wall of the mold cavity. After the material tube is completely adhered or applied to the inner wall of the mold cavity, maintain the molding pressure and start at the same time external water cooling. External water is cooled until it is consistent with the ambient temperature. Then the mold is demolded or released, the mold is removed, the two molds halves are separated again, and the formed balloon 12 is taken out. At this time, the balloon 12 has an expansion section 13 part and a non-expansion section part according to the shape of the mold. It is also possible to disregard the expansion and non-expansion parts, and restrict the non-expansion part after the balloon 12 is set to the preset position so that it cannot be expanded significantly. The core tube 11 is extruded, a thermoplastic polymer material is selected, and then extruded after melting to form a single-lumen or multi-lumen tube. According to the preset position of the balloon 12, a small hole 14 is punched in the core tube 11 using a catheter puncher. The balloon 12 is placed in a preset position, and the balloon 12 is fixed or secured on or over the core tube 11 by welding or glue bonding. When considering the use of the filamentous material 15, the filamentary material 15 should be a metal wire with less ductility (large modulus), one end fixed near the distal end of the core tube 11 (preferably the distal end of the balloon 12). The other end is fixed near the proximal end of the core tube 11 (preferably the proximal end of the balloon 12), and glue is used to bond the filamentous material 15 and the core tube 11 together.

The preparation method in the case of multiple balloons: firstly select a thermoplastic polymer material, melt it and extrude it into a barrel or material tube. Milling the balloon forming mold, the mold is divided into two halves, and the shape of the internal cavity after the two mold halves are spliced is consistent with the final outer contour of the single balloon 12. The spliced mold is placed on a balloon forming machine, and the material tube is placed in the cavity. Set the molding temperature, molding internal pressure and stretching rate, stretch and expand the material tube so that the outer wall of the final material tube is adhered or applied to the inner wall of the mold cavity. After the material tube is completely adhered or applied to the inner wall of the entire mold cavity, maintain the molding pressure and start at the same time external water cooling. External water is cooled until it is consistent with the ambient temperature. Then the mold is demolded or released, the mold is removed, the two mold halves are separated again, and the formed balloon 12 is taken out. At this time, the balloon 12 has an expansion section 13 part and a non-expansion section part according to the shape of the mold. It is also possible to disregard the expansion and non-expansion parts, and restrict the non-expansion part after the balloon 12 is set to the preset position so that it cannot be expanded significantly. The core tube 11 is extruded, and a thermoplastic polymer material is selected, melted, and extruded to form a multi-lumen tube having a number of cavities greater than or equal to the number of balloons 12 needed. According to the preset position of the balloon 12, a catheter puncher is used to punch holes 14 in the multi-lumen tube. The number of holes 14 is the same as the number of balloons used. The axial distance between two adjacent holes 14 should be slightly greater than the length of the balloon 12, preferably, the distance is the sum of the length of the balloon 12 and the predetermined gap between the balloons 12. A plurality of balloons 12 are placed in preset positions, and the balloons 12 are fixed on the core tube 11 by welding or adhesive bonding, respectively.

The manufacturing method also includes after fixing the balloon to the core tube, fixing one end of the filamentous material 15 near the distal end of the core tube 11, and fixing the other end near the proximal end of the core tube 11, and then attaching the filamentous material 15 to the core tube. The tube 11 is glued.

Although the embodiments of the present invention have been disclosed as above, they are not limited to the applications listed in the specification and embodiments. It can be applied to various fields suitable for the present invention. Other modifications can be easily implemented for those familiar with the art. Therefore, without departing from the general concept defined by the claims and equivalent scope, the present invention is not limited to the specific details and the illustrations shown and described herein.

The invention claimed is:

1. A balloon pulling device includes a core tube and a balloon part, wherein the core tube part has an axis and can inflate and discharge fluid to the balloon part covering the core tube, wherein an entire axis of the balloon part is elongated and centered on one side of the core tube axis and the balloon part comprises several expansion sections and a plurality of non-expandable parts located between the expansion sections, which are larger than the balloon after being filled with fluid, so that the entire balloon forms a bend naturally after inflation.

2. The balloon pulling device according to claim 1, wherein the core tube is flexible and has a plurality of cavities in it.

3. The balloon pulling device according to claim 1, wherein the surface of the core tube has at least one hole, or there is a corresponding hole for each expansion section.

4. The balloon pulling device of claim 1, wherein the balloon is wrapped or attached to the core tube.

5. The balloon pulling device of claim 1, wherein centering of the axis of the balloon part on one side of the core tube axis, during inflation expands the expansion sections to deviate them from the axis of the core tube part.

6. The balloon pulling device according to claim 1, wherein the core tube can be a plurality of independent core tubes, and each core tube individually controls the inflation and discharging of a plurality of balloon expansion sections to control the degree of bending; or one multi-lumen tube, each tube independently controls the inflation and discharging of several balloon expansion sections to control the degree of bending.

7. The balloon pulling device according to claim 1, characterized in that there are several balloons on the core tube, and each balloon has a plurality of expansion sections, so that each balloon can be bent independently.

8. The balloon pulling device according to claim 1, wherein the two ends of the balloon are connected with a wire-like material with low ductility, one end of the wire-like material is fixed near the distal end of the core tube, and the other end is fixed near the proximal end of the core tube.

9. The balloon pulling device according to claim 1, wherein the length of the expanded section of the balloon is greater than the outer diameter of the unexpanded state.

10. The balloon pulling device according to claim 1, wherein an adjacent distance between the expansion sections of the balloon is less than 0.2 times the length of the expansion section.

* * * * *